US012629049B2

(12) United States Patent
Pfister

(10) Patent No.: US 12,629,049 B2
(45) Date of Patent: May 19, 2026

(54) METHOD FOR AUTOMATIC POSITION DETERMINATION REVIEW AND OVERALL MEDICAL SYSTEM

(71) Applicant: Siemens Healthineers AG, Forchheim (DE)

(72) Inventor: Marcus Pfister, Bubenreuth (DE)

(73) Assignee: Siemens Healthineers AG, Forchheim (DE)

(*) Notice: Subject to any disclaimer, the term of this patent is extended or adjusted under 35 U.S.C. 154(b) by 165 days.

(21) Appl. No.: 18/426,539

(22) Filed: Jan. 30, 2024

(65) Prior Publication Data

US 2024/0252058 A1     Aug. 1, 2024

(30) Foreign Application Priority Data

Jan. 30, 2023     (DE) .................... 10 2023 200 709.6

(51) Int. Cl.
 A61B 5/06         (2006.01)
 A61B 6/00         (2024.01)
         (Continued)

(52) U.S. Cl.
 CPC ............ A61B 5/066 (2013.01); A61B 6/4441 (2013.01); G06T 7/74 (2017.01);
         (Continued)

(58) Field of Classification Search
 CPC ......... A61B 6/12; A61B 6/4441; A61B 5/066; A61B 34/20; A61B 6/547;
         (Continued)

(56) References Cited

U.S. PATENT DOCUMENTS

2016/0199148 A1* 7/2016 Maracaja-Neto .... A61B 1/0052
                                              600/424
2022/0156925 A1  5/2022 Bydlon
2024/0245458 A1* 7/2024 Roh ...................... A61B 34/32

OTHER PUBLICATIONS

Centerline Biomedical; FDA Cleared Endovascular Navigation Technology; https://www.centerlinebiomedical.com/; Date of Screenshot: Aug. 19, 2022; 7 pp.
(Continued)

*Primary Examiner* — Irakli Kiknadze
(74) *Attorney, Agent, or Firm* — Lempia Summerfield Katz LLC

(57)         ABSTRACT

A method for automatic position determination review during position tracking of an object inserted in a hollow organ of a patient by an electromagnetic tracking (EMT) system in the presence of an X-ray device with a movable acquisition system includes providing a registration of the EMT system to the acquisition system. A reference image of the hollow organ of the patient is provided, a registration of the reference image is provided to the acquisition system, a position of the object is determined by the EMT system, and an associated position on the reference image is determined. A plausibility criterion and/or a boundary condition is applied for reviewing a plausibility of the position determined by the EMT system based on the reference image. If the plausibility criterion and/or the boundary condition is violated, a position correction of the position determined by the EMT system and/or an alternative position determination is performed.

16 Claims, 3 Drawing Sheets

(51) Int. Cl.
*A61B 34/20* (2016.01)
*G06T 7/73* (2017.01)

(52) U.S. Cl.
CPC ................. *A61B 2034/2051* (2016.02); *A61B 2560/0223* (2013.01); *G06T 2207/10081* (2013.01); *G06T 2207/10116* (2013.01); *G06T 2207/30004* (2013.01)

(58) Field of Classification Search
CPC .... A61B 2560/0223; A61B 2034/2051; A61B 6/5217; A61B 6/4452; A61B 6/4021; A61B 6/488; A61B 6/5258; A61B 6/032; A61B 6/027; A61B 6/40; A61B 6/545; A61B 6/582; A61B 6/587; A61B 6/06; A61B 6/4007; A61B 6/5235; A61B 6/5264; A61B 6/584; A61B 6/588; A61B 6/583; A61B 6/035; A61B 6/0492; A61B 6/589; A61B 6/54; A61B 6/585; A61B 6/46; A61B 6/5205; A61B 6/501; A61B 34/10; A61B 34/37; A61B 34/30; A61B 34/25; A61B 34/32; A61B 2034/105; A61B 2034/102; A61B 2034/107; A61B 2034/104; A61B 2034/2055; A61B 2034/252; A61B 6/4241; G06T 7/74; G06T 2207/10116; G06T 2207/10081; G06T 2207/30004; G06T 7/0012; G06T 7/70; G06T 3/60; G06T 2207/30168; G06T 2207/20021; G06T 7/246; G06T 5/80; G06T 11/008; G06T 7/136; G06T 7/11; G06T 11/006; G06T 2207/30241; G06T 2207/10012; G06T 2207/20081; G06T 2200/04; G06T 2210/41; G06T 2211/421; G06T 5/50; G06T 2207/10064; G06T 2207/20221; G06T 7/30; G06T 2207/30056; G06T 2207/30024; G06T 2207/30008; G06T 11/005; G06T 2211/408; G16H 30/40; G16H 20/40; G16H 30/20; G06V 2201/03; G06N 3/08; G06N 20/00; G06F 3/013
USPC .................................................. 378/62, 4, 19
See application file for complete search history.

(56) References Cited

OTHER PUBLICATIONS

Schönepauck Annette; NDI Europe; "How Electromagnetic Tracking Works"; Feb. 7, 2022; URL:https://www.ndieurope.com/de/news/wie-funktioniert-elektromagnetisches-tracking; 1 pp.

Siemens Healthineers; EVAR in the Hybrid OR; https://www.siemens-healthineers.com/clinical-specialities/surgery/surgical-disciplines/vascular-surgery-equipment/evar-in-the-hybrid-or; 2024/01/25; 8 pp.

U.S. Food and Drug Administration; (FDA), Intra-Operative Positioning System (IOPS); Ref No. K190106; Jun. 24, 2019; 2 pp.

Zhong, Xia, et al. "A machine learning pipeline for internal anatomical landmark embedding based on a patient surface model." International journal of computer assisted radiology and surgery 14.1; 2019, https://doi.org/10.1007/s11548-018-1871-y; 13 pp.

* cited by examiner

FIG 1

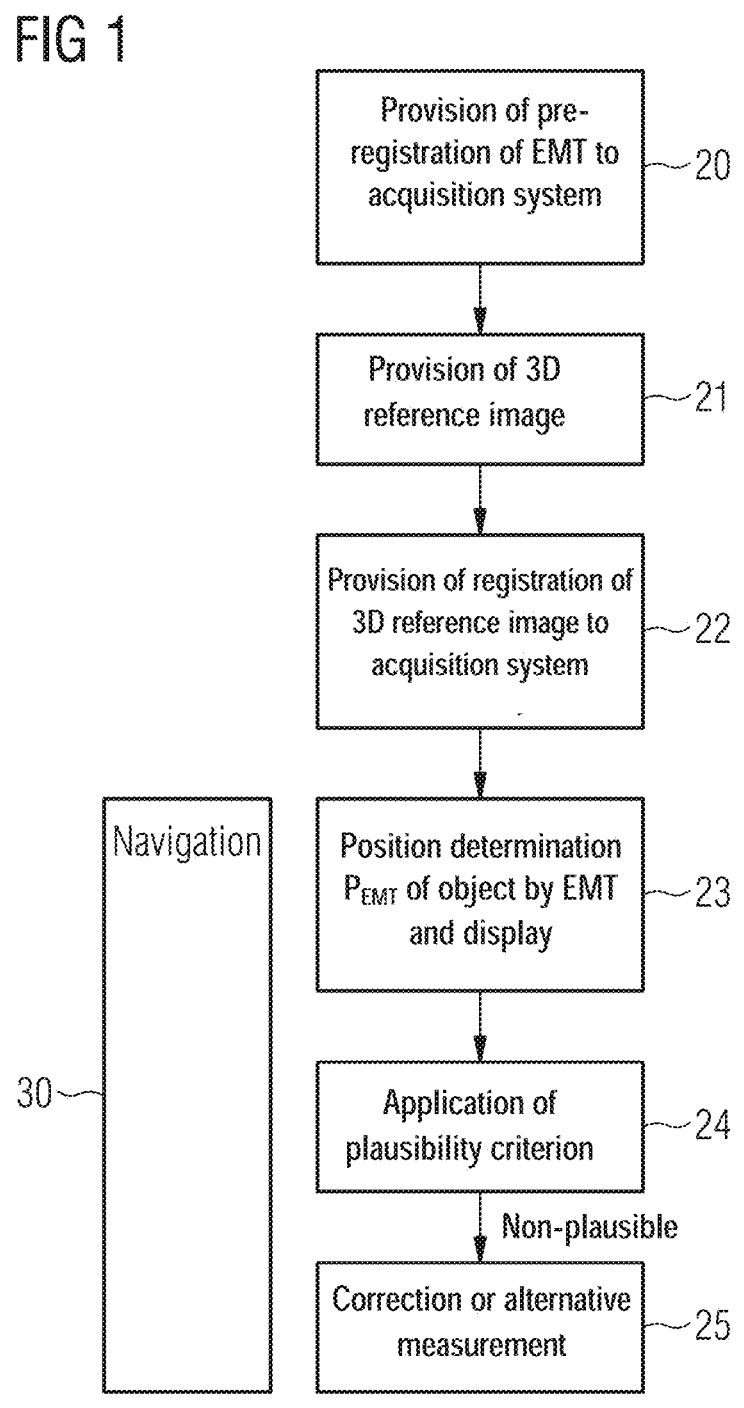

```
            ┌──────────────────────┐
            │   Provision of pre-  │
            │  registration of EMT to │──── 20
            │   acquisition system  │
            └──────────────────────┘
                       │
                       ▼
            ┌──────────────────────┐
            │    Provision of 3D   │──── 21
            │    reference image   │
            └──────────────────────┘
                       │
                       ▼
            ┌──────────────────────┐
            │Provision of registration of│
            │  3D reference image to │──── 22
            │   acquisition system  │
            └──────────────────────┘
                       │
                       ▼
┌───────────┐  ┌──────────────────────┐
│Navigation │  │ Position determination │
│           │  │ P_EMT of object by EMT │──── 23
│           │  │      and display      │
│    30 ────│  └──────────────────────┘
│           │             │
│           │             ▼
│           │  ┌──────────────────────┐
│           │  │    Application of    │──── 24
│           │  │  plausibility criterion │
│           │  └──────────────────────┘
│           │             │  Non-plausible
│           │             ▼
│           │  ┌──────────────────────┐
│           │  │ Correction or alternative │──── 25
│           │  │      measurement      │
└───────────┘  └──────────────────────┘
```

$P_{3D} = P_{EMT}$ $P_{EMT}$ $P_{3D}$

METHOD FOR AUTOMATIC POSITION DETERMINATION REVIEW AND OVERALL MEDICAL SYSTEM

This application claims the benefit of German Patent Application No. DE 10 2023 200 709.6, filed on Jan. 30, 2023, which is hereby incorporated by reference in its entirety.

BACKGROUND

The present embodiments relate to automatic position determination review during position tracking of an object inserted in a hollow organ of a patient by an electromagnetic tracking system in the presence of an X-ray device with a movable acquisition system.

In minimally invasive medical interventions, treatments (e.g., placement of a stent) or diagnoses (e.g., detection of stenoses) are performed using objects or instruments inserted into the body. Navigation of an instrument into a branch-off vessel of the hollow organ of the patient takes place by a guide wire or catheter being rotated and pushed forward at the puncture site (e.g., the groin), with a visual check generally taking place using fluoroscopy. To reduce the radiation exposure for patients and operators, use is made of radiation-free navigation methods (e.g., in cardiology and vascular surgery, such as electromagnetic tracking (https://www.centerline biomedical.com/) by an EMT system). An EMT system includes at least one sensor arranged on an instrument, a field generator, and an associated control and evaluation unit. Electromagnetically tracked instruments are co-visualized in a volume image (e.g., a CT acquisition) registered to the patient in order thus to enable navigation through the vascular system.

If the field generator of the EMT system and the C-arm (e.g., consisting of steel) come too close to one another, inhomogeneities occur in the magnetic field. Consequently, the accuracy of these methods is restricted, in extreme cases to the point where the EMT system is useless. It is possible, when using the EMT system, to move the C-arm completely out of the examination area or to calibrate different "fixed" C-arm field generator constellations (e.g., AP over the center portion of the patient); however, this is laborious and significantly delays the navigation procedure. Additionally, a warning system may be provided that outputs a signal when the C-arm approaches the field generator.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a method that reduces or prevents interference during EMT tracking by the acquisition system (e.g., the C-arm) of the X-ray device is provided. As another example, an overall system suitable for the performance of the method is provided.

The method of the present embodiments for automatic position determination review during position tracking of an object inserted in a hollow organ of a patient by an electromagnetic tracking system (EMT system; EMT) in the presence of an X-ray device with a movable acquisition system (e.g., a C-arm) includes the following acts: provision of a registration of the EMT system (EMT) to the acquisition system of the X-ray device, provision of a, for example, presegmented reference image (e.g., a 3D reference image) of the hollow organ of the patient, provision of a registration of the 3D reference image to the acquisition system of the X-ray device, position determination of the object by the EMT system (EMT) and determination of the associated position on the reference image (e.g., the 3D reference image), application of at least one plausibility criterion and/or one boundary condition for reviewing the plausibility of the position determined by the EMT system based on the reference image (e.g., the 3D reference image), and, if the at least one plausibility criterion and/or the boundary condition is violated, performance of a position correction of the position determined by the EMT system (EMT) and/or of an alternative position determination. Thanks to the method, an erroneous position determination of the EMT system generated, for example, by a C-arm may automatically and easily be reviewed during navigation of an object in a vascular system of the patient, and the error may be rectified quickly and accurately. The method does not require any manual intervention by an operator, who is thus able to concentrate attention on the patient and the navigation procedure. The number of faults and interruptions to the procedure is reduced, thus relieving the pressure on the operator and also the patient. Erroneous navigation procedures and erroneous diagnoses are reduced, and because the procedure takes less time, the X-ray dose and thus also the health risk for the individuals involved may be reduced.

In accordance with one embodiment, the at least one plausibility criterion includes a review as to whether the position and/or orientation and/or the dimensions of the object are inside a previously established area (e.g., inside the previously segmented hollow organ, inside the previously planned path, and/or inside a previously established roadmap). A plausibility criterion such as this may be established quickly, with little effort, and without additional measurements. The plausibility criterion may for example, be implemented by a simple software algorithm (e.g., image recognition). The operational sequence may for example, be as follows: the position of the object determined by the EMT system is superimposed or marked onto the 3D reference image, a processing unit containing image recognition software reviews the position and establishes (e.g., based on the segmentation) that the position is located outside the hollow organ, and consequently, the plausibility criterion that the position must be arranged inside the hollow organ is violated. Multiple plausibility criteria may also be used.

In accordance with a further embodiment, the reference image (e.g., the 3D reference image) is formed by a preoperative or intraoperative CT X-ray image or cone beam X-ray image or angiography X-ray image or planning image. Preoperative X-ray images are frequently acquired for an overview or for planning purposes (e.g., planning of the intervention or of the navigation path of the object) and are thus frequently already available without additional effort. In some cases, it may make sense to acquire intraoperative 3D X-ray images (e.g., in order to visualize the progress of therapeutic procedures). A virtual image (e.g., a simulated image or at least an image modified by augmented reality) may also be used. In some cases, it may also be sufficient to use a two-dimensional reference image (e.g., in the case of planning data).

In accordance with a further embodiment, there is also a presegmentation of the 3D reference image with respect to the hollow organ (e.g., with respect to the centerlines and surfaces of the hollow organ). Thanks to presegmentation, the preconditions for a plausibility review are already in place, so that this may be performed more quickly and with less effort. Thanks to presegmentation, it is possible to establish in advance where, for example, the hollow organs are located, so that the plausibility review here need only verify, for example, whether the object is located inside or outside the hollow organs.

In accordance with a further embodiment, the EMT system has at least one sensor arranged on the object, a field generator, and an associated control and evaluation unit. Such EMT systems are known and may be consulted and used without additional effort.

In accordance with a further embodiment, a signal or a warning is also output if the at least one plausibility criterion is violated. Thus, the operator may be notified that a problem has occurred. Thus, if necessary, the operative may respond to the violation of the plausibility criterion (e.g., to pause the navigation procedure or something similar) until a review has taken place. The operator may also perform a manual review.

In accordance with a further embodiment, a calibration factor K is used in connection with a position correction, for which the following applies: $P_{3D}(t)=K\cdot P_{EMT}(t)$, where $P_{3D}(t)$ is the actual position of the sensor at the time t, and $P_{EMT}(t)$ is the position of the sensor determined by the EMT system at the time t. This calibration factor may be determined, for example, by an alternative position determination for the object and then be used further, in order to correct non-plausible positions determined by the EMT system. The calibration factor may for example, be a simple factor, a two- or multi-dimensional function, a displacement vector, or another operator.

In accordance with a further embodiment, the calibration factor is determined by estimation. Thus, if it is established that the position of the object measured by the EMT system does not satisfy the plausibility criterion, then, for example, an estimation of the actual position may be performed. This may be done, for example, by assuming that the actual position is located, for example, inside the volume center of the 3D reference image or inside the center or the centerline of the hollow organ or at a position inside the hollow organ closest to the (EMT-)measured position. The calibration factor may then be determined from the estimated actual position of the object. A calibration factor determined in this way may be used, for example, for further measurements with the EMT system, in order to correct the position of the object measured by the EMT system.

As an alternative to position determination of the object by the EMT system, use may be made, for example, of one or, for example, two or more fluoroscopy acquisitions, an ultrasound measurement, a determination by measuring a length of an inserted catheter, or measurements based on RFIDs arranged on the object.

In accordance with a further embodiment, the calibration factor is calculated by calculation from the actual position of the object determined by an alternative position determination. This may easily be done using the formula $P_{3D}(t)=K\cdot P_{EMT}(t)$. Then, for the further measurements, the calibration factor determined in this way may be used in order to correct the measured position of the object (e.g., measured by the EMT system). This may be done, for example, until the position of the C-arm is changed.

In accordance with a further embodiment, in connection with the alternative position determination, at least two projection geometries are determined for the acquisition system, based on which the actual position of the object may be determined. The determination of the suitable projection geometries (e.g., angulations of the acquisition system) may be performed automatically, for example, by the system controller of the X-ray device using parameters. Such parameters may for example, be the distances between object (e.g., patient or hollow organ) and X-ray source/ detector, an X-ray voltage, an X-ray dose, collimator settings, collision avoidance criteria, or suitable reconstruction conditions. Thus, the projection directions of two projections may for example, differ sufficiently (e.g., by at least 5°) to be able to perform a unique 3D position determination. In this way, a very precise determination of the actual position of the object may be performed.

For example, the at least two determined projection geometries are, for example, suggested and/or taken up by the X-ray device, and at least two projection images are acquired with these projection geometries. This may be done automatically or in consequence of a manual input (e.g., confirmation) by an operator.

In accordance with a further embodiment, the method is, for example, performed during an endovascular aortic repair (EVAR) or a cardiological intervention or a neuroradiological intervention or an abdominal radiological intervention. Neuroradiological interventions may for example, include coiling of aneurysms or a thrombectomy; in cardiological interventions, use is, for example, made of stents, or CTOs (e.g., vascular occlusions) are treated. In abdominal radiology, the TACE is performed. These interventions in each case include navigation of an object in a hollow organ using X-ray monitoring. By using the method when employing an EMT system for position determination, errors in the position determination may easily be revealed and/or corrected, so that the interventions may be performed more safely and considerately for the patient.

The present embodiments also include an overall system for the performance of the above-mentioned method during navigation of an object inserted in a hollow organ of a patient. The overall system includes: an EMT system with at least one sensor arranged on an object, a field generator, and an associated control and evaluation unit, an X-ray device with a movable acquisition system, on which an X-ray source and an X-ray detector are mounted, a control system for the automatic activation of the method, and a processing unit for reviewing at least one plausibility criterion and/or one boundary condition with respect to the plausibility of a position determined by the EMT system based on a 3D reference image.

BRIEF DESCRIPTION OF THE DRAWINGS

FIG. 1 shows a view of acts of one embodiment of a method;

DETAILED DESCRIPTION

Figure 5:
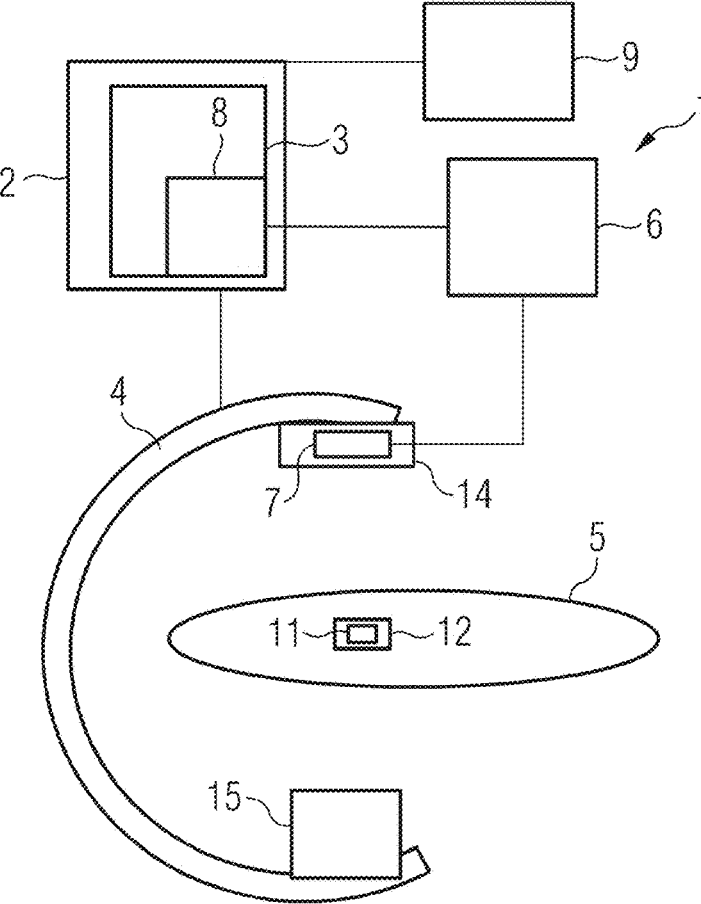
FIG. 5 shows an overall system for the performance of the method.

FIG. 1 shows an operational sequence of acts for the performance of a method. The method is at least partially performed during navigation 30 of an object through a hollow organ of a patient, for example. An overall system 1 suitable for this is shown in FIG. 5. The overall system 1 has an X-ray device 2 with a system controller 3 and a movable acquisition system 4, an EMT system, and a control system

8 for the automatic activation of the method. The acquisition system 4 may, for example, be formed by a C-arm, on which an X-ray source 15 and an X-ray detector 14 are mounted. The C-arm may, for example, be displaced in a translatory and rotational manner (e.g., into different positions; angulations or projection geometries/directions). The EMT system has at least one sensor 12, a field generator 7, and an associated control and evaluation unit 6. The sensor 12 is arranged on an object 11. The object 11 is located in a hollow organ (e.g., blood vessel, heart, lung) of a patient 5 and is moved or navigated therein automatically, semi-automatically, or manually, for example, by a guide wire. The object 11 may, for example, be a guide wire, a catheter, a stent, or an instrument.

Such semi-automatic or automatic navigation of an object 11 into a hollow organ may take place, for example, by motor-assisted rotation and forward movement of the guide wire or catheter; a visual check generally takes place using fluoroscopy acquisitions. In order to reduce the radiation exposure for patients and operators, use is made (e.g., in cardiology and vascular surgery) of radiation-free navigation methods such as electromagnetic tracking by the EMT system. The basic operating principle of the EMT system is as follows: in electromagnetic tracking, a variable low-intensity magnetic field is output by the field generator 7 that covers a particular measurement volume. If the sensor 12 moves inside the measurement volume, small currents are induced. These are amplified and digitalized.

Using the control and evaluation unit 6, the digitalized signals are measured, and the position and/or orientation of the sensor 12 (and thus of the object 11) are determined therefrom. If the field generator 7 and the acquisition system (e.g., in the form of the C-arm (partially) consisting of steel) come too close to one another, inhomogeneities occur in the magnetic field. Consequently, the accuracy of this measurement method is restricted, in extreme cases to the point where the EMT system is useless. The method of the present embodiments is provided in order to review a potentially erroneous position determination and to rectify the error quickly and simply. The method does not require any manual intervention by an operator, who is thus able to concentrate attention on the patient and the navigation procedure. Errors may be reduced, and the health risk for the patient may be reduced.

In the following, reference is chiefly made to the position of the object 11. Initially, the position of the sensor 12 is generally measured by the EMT system, but this may easily be converted due to the fixed arrangement on the object 11 (e.g., at the tip of the object). The orientation of the object 11 may also be easily determined, for example, if the exact shape and size of the object 11 and the arrangement of the sensor 12 are known.

In principle, the method may also be used for all EM-tracked interventions (e.g., during an endovascular aortic repair (EVAR) or a cardiological intervention or a neuroradiological intervention or an abdominal radiological intervention). Neuroradiological interventions may for example, include coiling of aneurysms or a thrombectomy; in cardiological interventions, use is, for example, made of stents, or CTOs (e.g., vascular occlusions) are treated. In abdominal radiology, the TACE is performed.

In a first act 20, a registration of the EMT system EMT to the acquisition system 4 of the X-ray device 2 is provided. Such registration is to be provided in order, during a position measurement, to be able to perform an assignment of the determined positions of the object to the reference system of the X-ray device (e.g., for displays on an X-ray image or similar). The registration may already be present prior to the commencement of the method, if, for example, the EMT system has already been assigned to the X-ray device and/or is structurally integrated (shown in FIG. 5), in which the field generator 7 is arranged on the X-ray detector 14. The registration may also be performed in connection with the method.

In a second act 21, a, for example, presegmented reference image (e.g., a 3D reference image) of a hollow organ 10 of the patient 5 is provided. Such a 3D reference image may for example, be formed by a preoperative volume image that was acquired by a computed tomography system or a cone beam X-ray device for the preparation of a medical (e.g., interventional and/or operational) procedure. In general, in advance of an interventional procedure, preoperative X-ray images are produced, so that it does not represent any additional effort to use these too. A volume image acquired during the procedure may also be used. Such a volume image may for example, be reconstructed from a series of projection images with different projection geometries (e.g., angulations). In some cases, it may also be sufficient to use a two-dimensional reference image.

A planning image (e.g., a virtual or simulated or partially augmented volume image) may also be used. Segmentation of the corresponding 3D reference image may already be present or may also be performed using known methods. The segmentation is, for example, performed or is present with respect to the mapped hollow organ of the patient; further structures (e.g., bones, organs, tissue boundaries, implants, etc.) may also be segmented. A hollow organ may for example, be segmented such that a centerline and/or a surface of the hollow organ is determined. As a result, a review of the plausibility of the position of the object or sensor may subsequently be performed more easily.

In a third act 22, a registration of the 3D reference image to the acquisition system of the X-ray device is provided. The registration is in the simplest case already present if the 3D reference image was, for example, acquired with the same X-ray device or if navigation planning was already performed based on the 3D reference image. If the registration is still not present, this is performed in connection with the method. This may for example, be performed based on images (e.g., using markers).

In a fourth act 23, a position determination of the navigated object 11 (e.g., with the sensor 12 affixed thereto) is performed based on the EMT system, for example, as described above by measurement and evaluation of currents induced by the navigation movement of the sensor 12 inside the variable magnetic field generated by the field generator 7. This is performed during the navigation 30 of the object 11. The evaluation may for example, by performed by the control and evaluation unit 6 of the EMT system. The (e.g., possibly incorrect) position of the object 2 determined by the EMT system is designated here as $P_{EMT}(t)$.

Figures 2, 3:
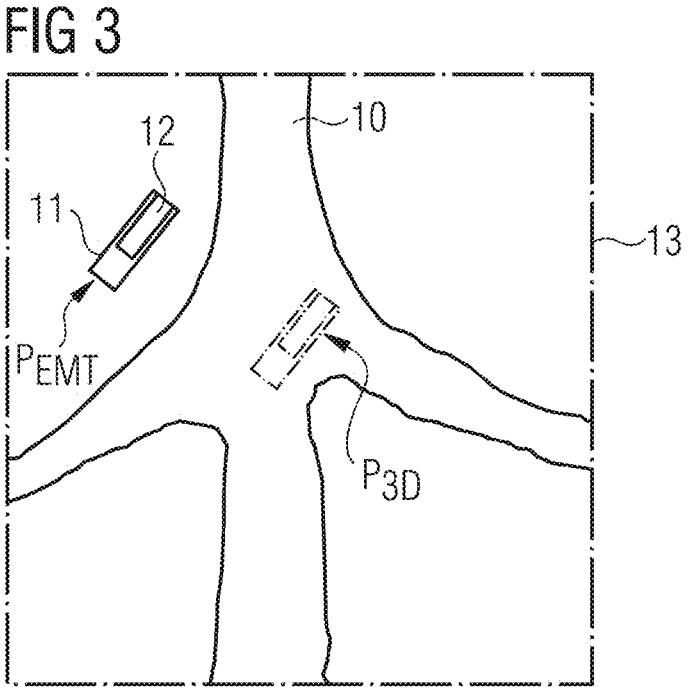
FIG. 2 shows a view of an object arranged in a hollow organ with a plausible position.
FIG. 3 shows a view of an object arranged in a hollow organ with a non-plausible position.

Thanks to the registration of the EMT system to the 3D reference image, the thus determined position $P_{EMT}(t)$ relative to the 3D reference image may be determined or displayed. This may be done, for example, by transmitting the position $P_{EMT}(t)$ to the processing unit 8 of the overall system. The position $P_{EMT}(t)$ may (but does not have to) be displayed on a display unit 9, for example, by superimposition, overlay, or marking in the 3D reference image (e.g., also in the form of the object 11). FIGS. 2 and 3 each show superimposition images 13, showing the hollow organ 10 of the 3D reference image with the position $P_{EMT}(t)$ of the object 11 (e.g., with the sensor 12) determined by the EMT system. In FIG. 2, the position $P_{EMT}(t)$ of the object 11 determined by the EMT system is located inside the hollow organ 10, and in FIG. 3, the position $P_{EMT}(t)$ of the object 11 determined by the EMT system is located outside the hollow organ 10.

In a fifth act 24, at least one plausibility criterion and/or one boundary condition for reviewing the plausibility of the position determined by the EMT system is then applied based on the 3D reference image. A simple plausibility criterion may for example, be that the object 11 (e.g., with the sensor 12) is to be located inside the segmented hollow organ (e.g., with respect of its position and/or dimensions). Previous planning for the intervention may also be used to establish the plausibility criterion, so that, for example, it is to be provided that the object 11 is located not only inside the hollow organ, but also in a particular area (e.g., established beforehand) of the hollow organ, at a particular distance away from a point, in a particular surrounding area of the previously planned path, or inside a previously established roadmap.

A plausibility criterion may also be linked to the orientation of the object 11. Two or more plausibility criteria may also be reviewed. The fifth act 24 may, for example, be carried out in that the processing unit 8 verifies (e.g., using an image recognition algorithm) whether the position of the object 11 $P_{EMT}(t)$ is located inside the segmented hollow organ. FIG. 2 shows that the position $P_{EMT}(t)$ of the object 11 determined by the EMT system is located inside the hollow organ 10, in which case it is then, for example, assumed that this is the correct position $P_{3D}(t)$. If the position of the object 11 $P_{EMT}(t)$ is not located inside the segmented hollow organ, a violation of the plausibility criterion is established. It is consequently assumed that the position $P_{EMT}(t)$ of the object 11 determined by the EMT system is not correct (e.g., $P_{3D}(t) \neq P_{EMT}(t)$; see, e.g., FIG. 3), and that this has come about due to interference to the magnetic field caused by the C-arm.

If the violation of at least one plausibility criterion is established, then subsequently, in a sixth act 25, an alternative position determination is performed and/or a position correction of the position determined by the EMT system (EMT) (e.g., "recalibration"). An alternative position determination of the position of the object 11 may, for example, simply be performed by two or more projection acquisitions of the X-ray device with different projection geometries (e.g., angulations of the acquisition system) and a 3D image of the object 2 and of its surrounding area reconstructed therefrom. The projection geometries necessary for an accurate reconstruction (e.g., the angulations of the acquisition system) may be determined beforehand and then input either automatically or after confirmation by an operator. Thus, the actual position $P_{EMT}(t)$ of the object 11 may be determined. Other alternative methods may also be used to determine the actual position of the object 11 (e.g., an ultrasound measurement, a measurement using RFID (providing the object 11 bears such an RFID), or a determination via the planning data in combination with the length of an inserted catheter or guide wire, on the end of which the object 11 is arranged).

Figure 4:
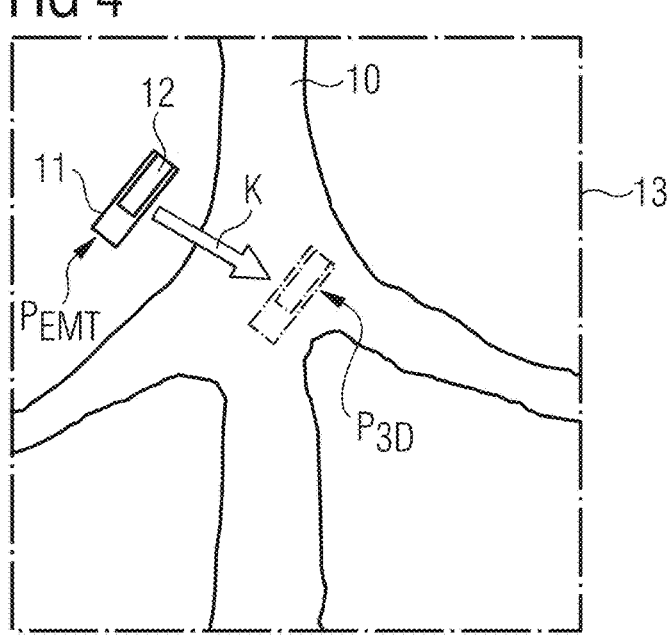
FIG. 4 shows a view of an object arranged in a hollow organ with a non-plausible position.

If a calibration factor K has already been determined from a previous alternative position determination of the object 11 with the acquisition system (e.g., C-arm) in the same position, for which $P_{3D}(t)=K \cdot P_{EMT}(t)$ applies, then, instead of the alternative position determination of the object 11 (or in addition thereto), a simple position correction may be performed using the calibration factor K in order to determine the actual position $P_{3D}(t)$ of the object 11. As a precondition for this, it is assumed that quasi-static interference to the magnetic field by the acquisition system is present. Such a position correction is, for example, shown in FIG. 4. Thanks to the calibration factor K, the position $P_{EMT}(t)$ incorrectly determined by the EMT system is corrected so that the actual position $P_{3D}(t)$ of the object 11 is obtained.

Accordingly, the calibration factor for the respective position of the acquisition system (C-arm) may be determined from the formula $P_{3D}(t)=K \cdot P_{EMT}(t)$ (e.g., during a first determination of the actual position $P_{3D}(t)$ of the object 11 (using alternative measurement methods)), so that this may be used for correction in the case of subsequent measurements. The calibration factor may also be determined by an estimation and used subsequently. If, for example, a calibration factor is determined (e.g., calculated or estimated as described) in each case for two or more different positions of the acquisition system, then, in the case of a further position that, for example, lies between the two or more positions of the acquisition system, a further calibration factor may be interpolated from the other calibration factors. An extrapolation of such a further calibration factor is also possible in the case of further positions arranged outside the other positions. An estimation may also take place based on planning data.

Besides the alternative position determination and/or position correction, a signal and/or a warning may also be output to the operator. Thus, for example, a display (e.g., flashing light, color display, text, image, etc.) may be output at the display unit 9, or an acoustic signal may be output by a microphone.

The fourth act 23 and the fifth act 24, and also the sixth act 25 if non-plausibility is determined, may be repeated several or many times (e.g., during an intervention with navigation 30), or may be performed continuously (e.g., until navigation 30 is completed or until the review is aborted (by the operator)). In this way, a correct position determination for the object 11 may always be provided.

The procedure may be carried out automatically, semi-automatically, or with manual inputs (e.g., inputs may be received for confirmation by an operator as to whether or which alternative position determination is to be performed). Automatic suggestions from the system controller regarding projection geometries may also be confirmed, selected, or rejected, for example. Further suggestions may then be made in the event of a rejection.

Instead of a 3D reference image, a 2D reference image or projection image may be used in simpler embodiments.

Independent of the grammatical term usage, individuals with male, female, or other gender identities are included within the term.

The present embodiments may be briefly summarized as follows: a method for automatic position determination review during position tracking of an object inserted in a hollow organ of a patient by an electromagnetic tracking (EMT) system in the presence of a X-ray device with a movable acquisition system (e.g., a C-arm) is provided for especially accurate positioning even in the event of possible interference, with the following acts: provision of a registration of the EMT system to the acquisition system of the X-ray device; provision of a, for example, presegmented 3D reference image of the hollow organ of the patient; provision of a registration of the 3D reference image to the acquisition system of the X-ray device; position determination of the object by the EMT system and determination of the associated position on the 3D reference image; application of at least one plausibility criterion and/or one boundary condition for reviewing the plausibility of the position determined by the EMT system based on the 3D reference image; and if the at least one plausibility criterion and/or the boundary condition is violated, performance of a position correction of the position determined by the EMT system and/or an alternative position determination.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may alternatively, be made to depend in the alternative from any preceding or following claim, whether independent or dependent. Such new combinations are to be understood as forming a part of the present specification While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for automatic position determination review during position tracking of an object inserted in a hollow organ of a patient by an electromagnetic tracking (EMT) system in a presence of an X-ray device with a movable acquisition system, the method comprising:

providing a registration of the EMT system to the movable acquisition system of the X-ray device;

providing a reference image of the hollow organ of the patient, the reference image being presegmented;

providing a registration of the reference image to the movable acquisition system of the X-ray device;

determining a position of the object by the EMT system and determining an associated position on the reference image;

applying at least one plausibility criterion, one boundary condition, or the at least one plausibility criterion and the one boundary condition for reviewing a plausibility of the position determined by the EMT system based on the reference image; and performing a position correction of the position determined by the EMT system when the at least one plausibility criterion is violated, when the one boundary condition is violated, or when the at least one plausibility criterion and the one boundary condition are violated, wherein the performing of the position correction of the position comprises using a calibration factor, for which the following applies:

$P_{3D}(t) = K \cdot P_{EMT}(t)$, where $P_{3D}(t)$ is an actual position of a sensor at a time t, and $P_{EMT}(t)$ is a position of the sensor determined by the EMT system at the time t.

2. The method of claim 1, wherein the movable acquisition system includes a C-arm.

3. The method of claim 1, wherein the reference image is a three-dimensional (3D) reference image.

4. The method of claim 1, wherein the applying comprises applying the at least one plausibility criterion, and wherein the at least one plausibility criterion comprises a review as to whether the position, an orientation, dimensions, or any combination thereof of the object is located inside a previously established area.

5. The method of claim 4, wherein the previously established area is inside a previously segmented hollow organ, inside a previously planned path, inside a previously established roadmap, or any combination thereof.

6. The method of claim 1, wherein the reference image is formed by a preoperative or intraoperative computed tomography (CT) X-ray image, a cone beam X-ray image, an angiography X-ray image, or a planning image.

7. The method of claim 1, wherein a presegmentation of the reference image is present with respect to the hollow organ.

8. The method of claim 7, wherein the presegmentation of the reference image is present with respect to centerlines and surfaces of the hollow organ.

9. The method of claim 1, wherein the EMT system includes at least one sensor arranged on the object, a field generator, and an associated control and evaluation unit.

10. The method of claim 1, wherein the applying comprises applying the at least one plausibility criterion, and wherein the method further comprises outputting a signal or a warning when if the at least one plausibility criterion is violated.

11. The method of claim 1, wherein the calibration factor is determined by estimation.

12. The method of claim 1, wherein the method is performed during an endovascular aortic repair (EVAR), a cardiological intervention, a neuroradiological intervention, or an abdominal radiological intervention.

13. A method for automatic position determination review during position tracking of an object inserted in a hollow organ of a patient by an electromagnetic tracking (EMT) system in a presence of an X-ray device with a movable acquisition system, the method comprising:

providing a registration of the EMT system to the movable acquisition system of the X-ray device;

providing a reference image of the hollow organ of the patient, the reference image being presegmented;

providing a registration of the reference image to the movable acquisition system of the X-ray device;

determining a position of the object by the EMT system and determining an associated position on the reference image;

applying at least one plausibility criterion, one boundary condition, or the at least one plausibility criterion and the one boundary condition for reviewing a plausibility of the position determined by the EMT system based on the reference image; and performing an alternative position determination when the at least one plausibility criterion is violated, when the one boundary condition is violated, or when the at least one plausibility criterion and the one boundary condition are violated, wherein the performing of the alternative position determination comprises determining at least two different projection geometries for the movable acquisition system, on the basis of which an actual position of the object is determinable;

determining a calibration factor by calculation from the actual position of the object determined by the alternative position determination; and performing a position correction of the position determined by the EMT system using the calibration factor.

14. The method of claim 13, wherein the at least two different projection geometries are suggested, taken up, or suggested and taken up, and at least two projection images are acquired with the at least two different projection geometries.

15. The method of claim 13, wherein the at least two different projection geometries are acquired with the X-ray device, and wherein a three-dimensional image of the object and a surrounding area of the object is reconstructed from the at least two different projection geometries.

16. A medical system for performance of automatic position determination review during position tracking of an object inserted in a hollow organ of a patient by an electromagnetic tracking (EMT) system in a presence of an X-ray device with a movable acquisition system, during navigation of the object inserted in the hollow organ of the patient, the medical system comprising:

the EMT system comprising at least one sensor arranged on the object, a field generator, and an associated control and evaluation unit;

an X-ray device comprising a movable acquisition system, on which an X-ray source and an X-ray detector are mounted; and one or more processors configured for automatic activation of performance of the position determination review, the performance of the position determination review comprising:

provision of a registration of the EMT system to the movable acquisition system of the X-ray device;

provision of a reference image of the hollow organ of the patient, the reference image being presegmented;

provision of a registration of the reference image to the movable acquisition system of the X-ray device;

determination of a position of the object by the EMT system and determination of an associated position on the reference image;

application of at least one plausibility criterion, one boundary condition, or the at least one plausibility criterion and the one boundary condition for review of a plausibility of the position determined by the EMT system based on the reference image; and performance of a position correction of the position determined by the EMT system when the at least one plausibility criterion is violated, when the one boundary condition is violated, or when the at least one plausibility criterion and the one boundary condition are violated, wherein the performing of the position correction of the position comprises using a calibration factor, for which the following applies:

$P_{3D}(t) = K \cdot P_{EMT}(t)$, where $P_{3D}(t)$ is an actual position of a sensor at a time t, and $P_{EMT}(t)$ is a position of the sensor determined by the EMT system at the time t.

* * * * *